US007815929B2

(12) United States Patent
Muni et al.

(10) Patent No.: US 7,815,929 B2
(45) Date of Patent: Oct. 19, 2010

(54) CONTAINER AND KIT FOR THE PREPARATION, STORAGE AND DISPENSING OF COMPOUNDED SUPPOSITORIES

(75) Inventors: Indu Muni, North Reading, MA (US); Gita Muni, North Reading, MA (US); Dilip Patel, Wellesley, MA (US); Peter Mione, Malden, MA (US); Denis Morin, Canterbury, CT (US)

(73) Assignee: CutisPharma, Inc., Woburn, MA (US)

( * ) Notice: Subject to any disclaimer, the term of this patent is extended or adjusted under 35 U.S.C. 154(b) by 49 days.

(21) Appl. No.: 12/207,957

(22) Filed: Sep. 10, 2008

(65) Prior Publication Data

US 2009/0028964 A1 Jan. 29, 2009

Related U.S. Application Data

(63) Continuation of application No. 11/093,178, filed on Mar. 29, 2005, now Pat. No. 7,434,690.

(60) Provisional application No. 60/566,696, filed on Apr. 30, 2004.

(51) Int. Cl.
*A61F 13/00* (2006.01)
*A61K 31/40* (2006.01)

(52) U.S. Cl. ......................... 424/433; 53/454; 424/436; 424/659; 514/420

(58) Field of Classification Search ................. 206/529, 206/562, 570–572; 424/400, 433, 436, 443, 424/659; 53/453, 454; 249/74, 134, 141; 514/177, 282, 420

See application file for complete search history.

(56) References Cited

U.S. PATENT DOCUMENTS

| | | | | |
|---|---|---|---|---|
| 1,749,996 | A * | 3/1930 | Brush | 206/529 |
| 2,012,535 | A * | 8/1935 | Herrold | 206/529 |
| 2,612,261 | A * | 9/1952 | Percopo | 206/529 |
| 2,980,248 | A * | 4/1961 | Embring | 249/121 |
| 3,059,766 | A | 10/1962 | Jordt | |
| 3,113,672 | A * | 12/1963 | Brown | 249/121 |
| 4,108,309 | A | 8/1978 | Bronner | |
| 4,174,040 | A * | 11/1979 | Wang | 206/529 |
| 4,537,311 | A * | 8/1985 | Wilkinson et al. | 206/529 |
| RE34,133 | E | 11/1992 | Thorne | |
| 5,640,859 | A | 6/1997 | Fromm | |
| 6,645,475 | B2 * | 11/2003 | Franklin et al. | 424/65 |

* cited by examiner

*Primary Examiner*—Luan K Bui
(74) *Attorney, Agent, or Firm*—Wolf, Greenfield & Sacks, P.C.

(57) ABSTRACT

A container suitable for the preparation, storage and dispensing of compounded suppositories is provided. Methods of preparing, storing and dispensing compounded suppositories utilizing such a container and related kits are also provided.

5 Claims, 8 Drawing Sheets

CONTAINER AND KIT FOR THE PREPARATION, STORAGE AND DISPENSING OF COMPOUNDED SUPPOSITORIES

RELATED APPLICATIONS

This application is a continuation application of U.S. Ser. No. 11/093,178, filed Mar. 29, 2005, now U.S. Pat. No. 7,434, 690 which claims priority under 35 U.S.C. §119(e) to U.S. Provisional Application Ser. No. 60/566,696, filed Apr. 30, 2004 which is herein incorporated by reference in its entirety.

FIELD OF THE INVENTION

The present invention relates generally to a container suitable for the preparation, storage and dispensing of compounded suppositories, and method of preparing, storing and dispensing compounded suppositories utilizing such a container.

BACKGROUND OF INVENTION

Suppositories are a solid dosage form of medication, dietary supplement or botanical extract that can be delivered internally to a patient, human or animal, in situations where it is not desirable for the patient to take the dosage orally, parenterally or when a local effect is desired by insertion of the solid dosage form directly to the affected area of the body. Known types of suppositories include rectal, vaginal and urethral suppositories. Compounded suppositories are dosage forms that are prepared by physicians, pharmacists, technicians, paramedic personnel and the like to meet the specific requirements of an individually prescribed dosage. A compounded suppository normally consists of one or more drugs mixed with a base compound which are absorbed within the body after insertion into the body cavity. The compounding of suppositories refers to the preparation, mixing, assembling, and packaging of a solid dosage drug or the like, usually based on a medical prescription ordered by a physician.

Typically, compounded suppositories are created in a mold. The mold includes one or more mold cavities sized and shaped based on a desired dosage amount and location of the body where the suppository is to be received. In preparing the suppositories, typically a suppository base compound is melted and then one or more drugs are added to the melted base, creating a mixture that is poured into each of the suppository cavities of the mold. Alternatively, one or more drugs may be dissolved or suspended in a base compound, creating a drug/base mixture that is then melted and poured into each of the mold cavities. The suppositories are then cooled to solidify the drug/base mixture so that the solidified suppository may be removed from the mold for future dispensing to a patient.

Suppository molds may include anywhere from a few cavities for the formation of suppositories up to in excess of 100 cavities, depending upon the size of the mold and the dosage amount requirements. Molds commonly used for the preparation of suppositories include those made out of metal, such as an aluminum alloy, brass or a plated metal. Metal molds often consist of two mold halves with cavities formed in each mold half such that when the mold halves are placed together to form a single mold and the cavities from the two halves are aligned, the desired shape of the suppository is formed in the cavity. These metal molds are lubricated and chilled prior to adding the drug/base mixture to facilitate the formation of the suppositories and the subsequent removal of the suppositories from the metal mold.

After formation of the suppositories and removal of the suppositories from the metal mold, the mold must be cleaned prior to subsequent use so that residue from one batch of suppositories does not affect the dosage amount of subsequent suppository batches. Another reason why the mold must be cleaned after each use is to ensure the desired quality of the subsequent suppository composition is maintained, especially if a different suppository composition is prepared in the subsequent application. Additionally, after the individual suppositories are prepared in a metal mold, they are typically manually removed and stored, in an unprotected form, in a container that is then passed to a patient under prescription. The patient would then manually remove an individual dosage from the container of suppositories for administration. With this unprotected group storage and manual handling of the suppository at the preparation and dispensing phases, there lies an ongoing risk that the suppository dosage quantity or quality could be adversely affected by breakage of portions of the suppository or partial melting of the suppository in the hands of the preparer or end user.

Suppositories are alternatively prepared and stored in disposable plastic shell containers that are often connected in strip form for individual dispensing by a patient. These plastic shells are commonly made of a relatively soft plastic such as polystyrene. A series of shell containers may be laid out in strip form so that each of the containers may be filled with a drug and base mixture to form a suppository. The strip of plastic shells may include perforated sections between the shell containers so that an individual suppository dosage may be manually separated from the rest of the strip for administration, followed by disposal of the plastic shell container.

While these plastic shell containers allow for the preparation, storage and dispensing of compounded suppositories in a single container, they are not without disadvantages. Among the disadvantages of disposable plastic shells is that the plastic shell is generally pliable and thus easily deformable, which can impede the retention of a desired shape of the shell container and adversely affect the dosage amount or physical quality of the suppository itself. For example, a suppository within a plastic shell that has been partially dented or compressed may result in less than the complete suppository quantity being removable from the shell, which would result in less than the desired dosage of medication being available and possible difficulty in administering the suppository due to an altered physical structure of the suppository.

SUMMARY OF THE INVENTION

The invention in some aspects relates to a device for the preparation, storage, and/or dispensing of compounded suppositories, and a method for preparing, storing, and/or dispensing suppositories using such a device.

In one aspect of the invention, a container for suppositories comprises a base having a substantially planar surface with a plurality of surface openings. The base also comprises a plurality of hollow members, each protruding from the base at one of the plurality of surface openings, each of the plurality of hollow members having a first end comprising a first member opening coincident with one of the plurality of surface openings, and a second end comprising a second member opening and a protective end cover removably coupled to the second end to cover the second member opening. The container also comprises a base support coupled to the base and supporting the base relative to a support surface.

In another aspect of the invention, a device for supporting compounded suppositories comprises a substantially planar surface comprising a plurality of surface openings, each of the plurality of surface openings defining a first end of a hollow member that extends from the substantially planar surface to a second end of the hollow member. The base also comprises a support member to support the substantially planar surface in relation to a support surface, wherein the support member defines a boundary of the substantially planar surface.

In a further aspect of the invention, a method of preparing compounded suppositories for use by an end user comprises providing a container having a surface with a plurality of openings dispersed across the surface, each of the openings forming a first end each of a plurality of hollow members, each of the hollow members extending from the surface to a second end of the hollow elongated member. The method further comprises combining at least one drug and at least one suppository base, and adding a suppository mixture of at least one drug and at least one suppository base to the surface of the container. The method also comprises spreading the suppository mixture across the surface such that the mixture falls through the plurality of openings dispersed across the surface and into the plurality of hollow members, forming a plurality of compounded suppositories, and storing the compounded suppositories in the container for dispensing by an end user.

In still another aspect of the invention, a kit for preparing compounded suppositories for individual application comprises a container comprising a surface having at least one opening and a plurality of hollow members that each protrude from one of the plurality of surface openings to an end portion of the hollow members, the plurality of hollow members adapted to contain compounded suppositories. The kit also comprises a plurality of caps, each of the plurality of caps removably coupled to the end portion of one of the plurality of hollow members, and instructions for preparing the compounded suppositories. In one embodiment, the kit further comprises a container top cover and/or a guide plate.

BRIEF DESCRIPTION OF THE DRAWINGS

Aspects of the invention are described in connection with the following illustrative non-limiting drawings in which like numerals reference like elements, and wherein.

DETAILED DESCRIPTION

Figure 1:
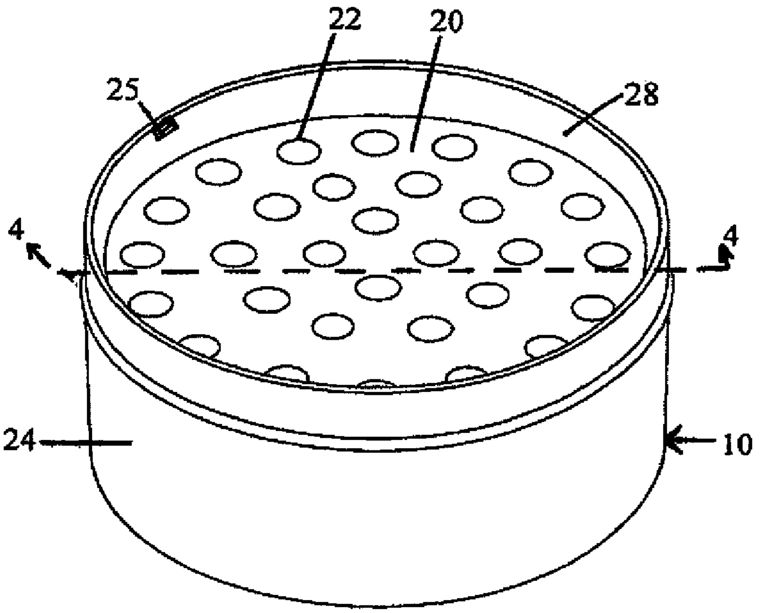
FIG. 1 is a perspective top view of a container according to one embodiment of the invention.

The present invention is directed in some aspects to a container for, and method of, preparing, storing and/or dispensing compounded suppositories. It should be appreciated that the invention is not limited to the specific container configuration and methods of preparing, storing and/or dispensing described below. The container could be constructed and arranged, and the suppositories prepared, stored and dispensed, in any of numerous ways within the scope of the present invention.

In one embodiment, the container is a device that facilitates the preparation, storage and dispensing of one or more compounded suppositories. The container may be constructed so as to minimize the need for manual handling of individual suppositories during the preparation, storage or dispensing phases until a patient or one who administers the suppository is ready to place the suppository into the body. The container may also be constructed and arranged such that the integrity of each of one or more suppositories is maintained in a protective hollow member that is integral with the container and that defines the external shape of the suppository. Additionally, the container may be constructed from a sturdy, lightweight material such as a plastic material that is not susceptible to collapsing or permanent deformation during manipulation of the container. One possible material suitable for such a container would be polypropylene. Other plastics, for example polyvinyl, as well as nonplastic materials such as a metal alloy could be used to construct the container of the present invention, and are also within the scope of the invention. The container may also be designed to be disposable after the creation of a single set or batch of suppositories.

Suppositories are solid dosage forms housing medicaments formulated for administration of medicine through the rectum, vagina or urethra that melt, soften or dissolve in the body cavity. Suppositories assume a variety of shapes and sizes. For instance, rectal suppositories are cylindrical or conical and tapered or pointed at one end. They generally weigh approximately 2 g and are about 1-1.5 inches long. Vaginal suppositories are available in various shapes, e.g., ovoid or globular, and weigh approximately 2-5 g each. Urethral suppositories, are usually about 5 mm in diameter and 50 mm in length for females and 125 mm in length for males, with weights being 2 g for female and 4 g for male. All sizes are smaller for infants and children. The medicament is incorporated into a base such as cocoa butter which melts at body temperature, or into one such as glycerinated gelatin or PEG which slowly dissolves in the mucous secretions.

In general, when formulating suppositories, the pharmacist should consider whether the desired effect is to be systemic or local, the route of administration (rectal, vaginal or urethral) and whether a rapid or a slow and prolonged release of the medication is desired. The selection of a suppository base is dependent upon a number of physicochemical variables, including the solubility characteristics of the drug. Factors such as the presence of water, hygroscopicity, viscosity, brittleness, density, volume contraction, incompatibilities, rate of drug release, pharmacokinetics and bioequivalence may be considered. Such factors are known to those of skill in the art. For example, the presence of water, or using water to assist in incorporating an active drug, generally should be avoided in the preparation of suppositories.

The container of the present invention may be used in the preparation, storage and/or dispensing of suppositories that include any number of types of commercially available drugs, salts or derivatives thereof. For purposes of this disclosure, the term "derivatives" refers to compounds having substantially similar pharmacological activity to the drug. By "substantially similar," what is meant is at least 75% of the drug activity, preferably at least 80% of the drug activity, more preferably at least 85% of the drug activity, even more preferably at least 90% of the drug activity, and still more preferably at least 95% of the drug activity. Derivatives will also share some structural similarity with the drug. Among the drugs or salts that may be compounded in a suppository dosage form are: Acetaminophen, Acetylsalicylic acid, Alum, Alprolazm, Aminophylline, Amoxicillin, Barbital, Benzoic acid, Benztropine, Belladonna Extract, Bisacodyl, Bismuth subgallate, Bismuth Carbonate, Bismuth Salicylate, Bismuth Subnitrate, Boric acid, Carbamezapine, Chloral hydrate, Chlorpromazine, Clindamycin, Cocaine, Dexamethasone, Diazepam, Diclofenac, Digitalis Extract, Diphenhydramine, Glycerin, Haloperidol, Ichthammol, Iodoform, Menthol, Metoclopramide, Morphine, Metronidazole, Miconazole, Naproxen, Nitroglycerin, Opium, Phenol, Potassium bromide, Potassium iodide, Paraffin, Phenobarbital, Procaine, Prochlorparazine, Promethazine, Quinine, Resorcinol, Salbutamol, Sodium bromide, Spermaceti, Sulfathiazole, Sulfasalazine, Tannic acid, Testosterone, Vancomycin, Witch Hazel extract, Zinc oxide, Zinc oxide with Lidocaine, Zinc sulfate, Hydrocortisone, Hydrocortisone with Lidocaine, Lidocaine, Ketoprofen, Ibuprofen, Phenytoin, Gabapentin, Klonazepam, Mesalamine, Prednisone, Indomethacin, Progesterone, Estrone, Estradiol, Estriol, Carbazepine, Ordansterone, Valporic acid, Hydromorphone, Ergot alkaloids, Ergotamine with Caffeine, Caffeine citrate, Oxycodone, Clotrimazole, Fluconazole, Econazole, Tinidazole, Nystatin, Ketocazole, Ltraconazole, Amphotercin, Secobarbital, Phenobarbital, Flucotisone, Budenoside, Nitrofurazone, Sucralfate, Piroxicam or various combinations thereof. Any other drugs useful in compounded suppositories are encompassed by the invention.

These drugs, salts or derivatives are available commercially from many different sources, such as Paddock Laboratories, St. Paul, Minn.; Professional Compounding Centers of America, Houston, Tex.; Medisca, Inc., Plattsburgh, N.Y.; Gallipot, Inc., St. Paul, Minn.; and Spectrum Pharmacy Products, Tucson, Ariz.

It should be understood that the above described drugs, salts and derivatives are exemplary and not an inclusive list of possible drugs, salts or derivatives that may be compounded. Additionally, the use of the term "drug" within this disclosure is intended to encompass any of the drugs, salts, derivatives thereof dietary supplements or botanical extracts anticipated by one of skill in the art that may be compounded using the container of the present invention.

Useful suppository bases are those that are stable, nonirritating, chemically and physiologically inert, compatible with a variety of drugs, melt or dissolve in bodily fluids, stable during storage, able to incorporate aqueous and oily liquids, capable of melting and solidifying over a narrow temperature range, not bind or otherwise interfere with the release or absorption of drug substances and be aesthetically acceptable. The ideal suppository base should also dissolve or disintegrate in the presence of mucous secretions or melt at body temperature to allow for the release of the medication. Suppository base composition plays an important role in both the rate and extent of release of medications.

Suppository bases are often classified according to their composition and physical properties, such as oleaginous (fatty) bases and water soluble or miscible bases. Oleaginous bases include but are not limited to Theobroma Oil or cocoa butter and synthetic triglyceride mixtures. At ordinary room temperatures of 15° to 25° C., oleaginous bases are generally a hard, amorphous solid, but at 30° to 35° C., i.e., at body temperature, they melt to a bland, nonirritating oil. In general these bases should only be heated to temperatures below 35° C. to avoid conversion to a metastable structure that melts in the 25° to 30° C. range.

Synthetic triglycerides, which consist of hydrogenated vegetable oils, are generally advantageous because they do not exhibit polymorphism. These bases include for example, but are not limited to Fattibase®, a single entity base that consists of triglycerides from palm, palm kernel, and coconut oils, Wecobee®, a series of bases (Wecobee FS, M, R, and S) that are all made from triglycerides of coconut oil but all having different melting point ranges, Dehydag®, Hydrokote®, Suppocire®, and Witepsol®.

Water soluble or miscible bases are made from glycerinated gelatin or polyethylene glycol (PEG) polymers. Glycerinated gelatin is suitable for use with a wide range of medicaments including alkaloids, boric acid, and zinc oxide. They are translucent, resilient, gelatinous solids that tend to dissolve or disperse slowly in mucous secretions to provide prolonged release of active ingredients.

PEG polymers are chemically stable, nonirritating, miscible with water and mucous secretions, and can be formulated, either by molding or compression, in a wide range of hardness and melting point. PEG polymers may be used singly as suppository bases but, more commonly, formulas call for compounds of two or more molecular weights mixed in various proportions as needed to yield a finished product of satisfactory hardness and dissolution time.

Table I sets forth a list of commonly used bases, which are commercially available for compounding suppositories and could be used with the container of the present invention to compound one or more of the drugs, salts or derivatives listed above into suppository dosage form.

TABLE I

Commonly Used Bases

| TRADE/COMMON NAME | INGREDIENTS | MANUFACTURER/ SUPPLIER |
|---|---|---|
| PCCA Base MBK ™ | Fatty Acid Base | PCCA* |
| PCCA Base A ™ | Polyglycol 1450 MW, NF | PCCA* |
| PCCA Base F ™ | Synthetic Cocoa Butter | PCCA* |
| Wecobee ® M, R, S, W | Vegetable Oil, Hydrogenated | Stepan Company, Northfield, IL |
| Witepsol ® H12, H15, W35 | Vegetable Oil, Hydrogenated | Stepan Company, Northfield, IL |
| Hydrokote ® M | Vegetable Oil, Hydrogenated | Abitec Corporation, Columbus, OH |
| COA Base | Fatty Acid Base | Spectrum Pharmacy Products, Tucson, AZ |
| Supposibase | PEG/Vegetable Oil | Spectrum Pharmacy Products, Tucson, AZ |
| Base A, B, D | Polyethylene Glycols | Spectrum Pharmacy Products, Tucson, AZ |
| Polybase | Polyethylene Glycol Blend | Gallipot, Inc., St. Paul, MN |

*Professional Compounding Centers of America, Inc., Houston, TX

Figure 2:
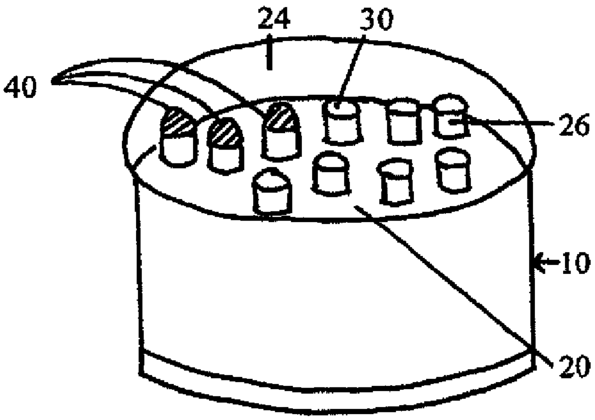
FIG. 2 is a perspective bottom view of the container of FIG. 1.
Figure 3:
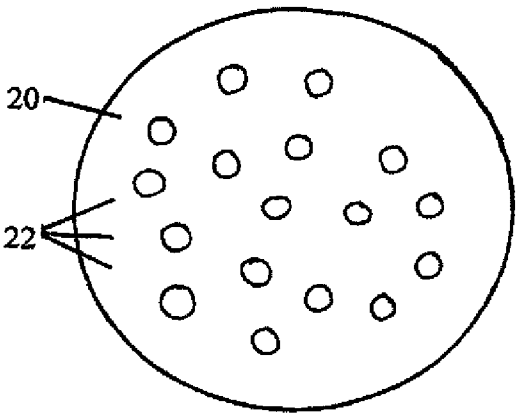
FIG. 3 is a top plan view of the container of FIG. 1.

FIGS. 1, 2 and 3 depict an illustrative embodiment of a suppository container incorporating aspects of the present invention. The container 10 may be used for the preparation, storage and/or dispensing of compounded suppositories. The container 10 may include a base 20 that has a plurality of surface openings 22 on the surface of the base 20, and a base support 24, coupled to the base 20 that may act as a support member to assist in keeping the container 10 and the base 20 in a position relative to a support surface. In the embodiment of FIG. 1, the container is generally cylindrical in shape, with the base support 24 forming a generally cylindrical shell that defines much of the overall shape of the container 10. The base support 24, as can be seen in further detail in FIG. 2, may take the form of a tubular-like structure that projects in a vertical direction from a horizontal base 20. However, it should be understood that the shape of the container 10 may take any of numerous forms as may be anticipated by one of ordinary skill in the art. For example, a container that is generally rectangular, triangular, oval or other shapes is anticipated within the scope of the present invention. Likewise, the shape of the base support 24 itself may also take other forms and shapes consistent with the scope of this invention. For example, in another embodiment the base support may take the form of a shelf-like projection from the body of the container, which could be used to support the container by resting the shelf-like projection on a suppository container holder separate from the container. Alternatively, the base support may comprise multiple elements such as legs that support the base on a surface or hooks to hang or suspend the container.

In another embodiment, the container may include a container top cover that is sized to generally match the dimensions of the top of the container 10. The top cover may be placed over the surface of the base 20 after the suppository preparation phase in order to protect the plurality of surface openings 22, and any suppositories stored therein, from external contaminants. The container top cover may be secured to the container by frictionally engaging, snap fitting or screw fitting the top cover to the external perimeter of a barrier rim 28 (discussed in further detail below) so that the top cover does not physically touch the base, but is held in place over the base and positioned a certain distance from the surface of the base. Alternatively, in an embodiment of the container that does not include a barrier rim 28, a top cover may be placed directly onto the surface of the base 20 and secured to the container by frictionally engaging, snap fitting or screw fitting the top cover to the container 10. It should be understood that other means to secure the top cover to the container, as known by those of skill in the art, are also within the scope of this invention. The top cover may be made of a plastic material, such as polypropylene, or other materials as known by those of skill in the art.

Figure 11:
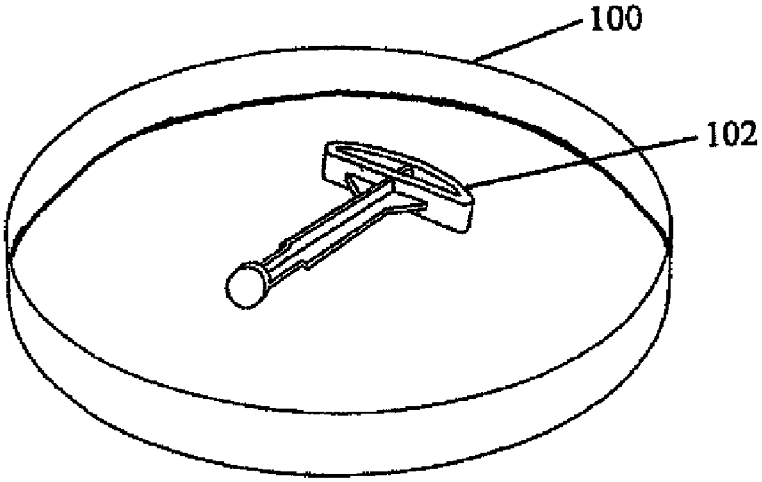
FIG. 11 is a perspective view of A 30-unit suppository mold cover with suppository dispensing tool attached.

The top cover may optionally be a suppository mold cover (100) with a suppository dispensing tool (102) attached such as the one shown in FIG. 11.

In another embodiment, the base 20 has a planar or substantially planar surface that extends across one side, which may be described as a top side, of the container 10. As shown in further detail in the embodiment of FIG. 3, the base 20 may include a plurality of openings 22 on the surface 20. The base 20 may be circular in shape with surface openings 22 that are likewise circular. However, the base 20 and the surface openings 22 may each take any number of shapes as may be anticipated by one of ordinary skill in the art. For example, the base may have a hexagonal or other polygonal shape while the openings may be oval. Any of numerous other combinations of shapes are also anticipated as being within the scope of the invention. Additionally, in another embodiment, the base 20 may have a substantially planar surface only in proximity to the surface openings 22, while other portions of the base (e.g., closer to the perimeter of the base) may not be planar at all, but instead may be angled, sloped, curved or include other such nonplanar surfaces as may be contemplated by one of skill in the art.

Figure 10:
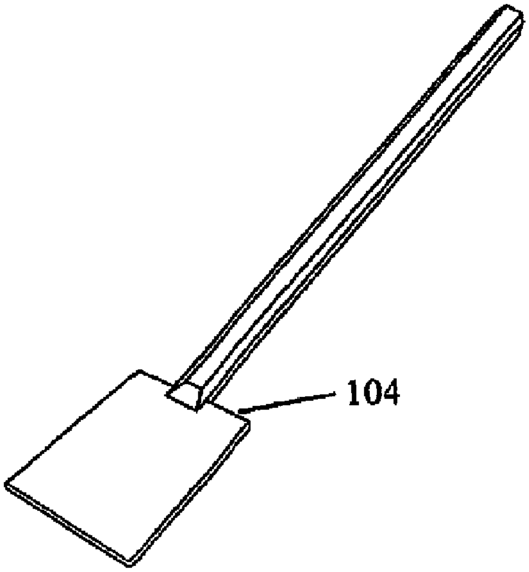
FIG. 10 is a perspective view of a stirrer.

The device or kit may also include a stirrer for mixing the suppository base and active agent. An exemplary stirrer (104) is shown in FIG. 10.

Further, the base 20 may also include one or more base dividers positioned on the surface of the base 20 that separate one portion of the surface of the base 20 from one or more other portions of the surface of the base 20. Such base dividers may facilitate the preparation of more than one drug/base mixture in the container 10 at the same time.

Furthermore, while FIG. 3 shows an exemplary number of thirty surface openings 22 dispersed across the surface of the base 20, any number of openings may be provided and dispersed across the base 20 consistent with the present invention. A container 10 may include a base 20 having a number of surface openings 22 ranging from a singe opening to over a hundred openings, depending on the dosage needs for a particular type of suppository. Typical numbers of openings useful for preparing compounded suppositories include, for example, 7, 14, 30 or 90. In another embodiment, the surface of the base 20 may include optional markings (for example, "1", "2", "3" . . . etc.; or "Day 1", "Day 2", "Day 3" . . . etc.) in the vicinity of one or more of the surface openings 22 that may pose as reminders for an end user as to when to dispense a particular suppository. An "end user" may refer to a preparer of the suppositories such as a pharmacist or a medical worker or optionally may be the patient who will administer the product.

Figure 9:
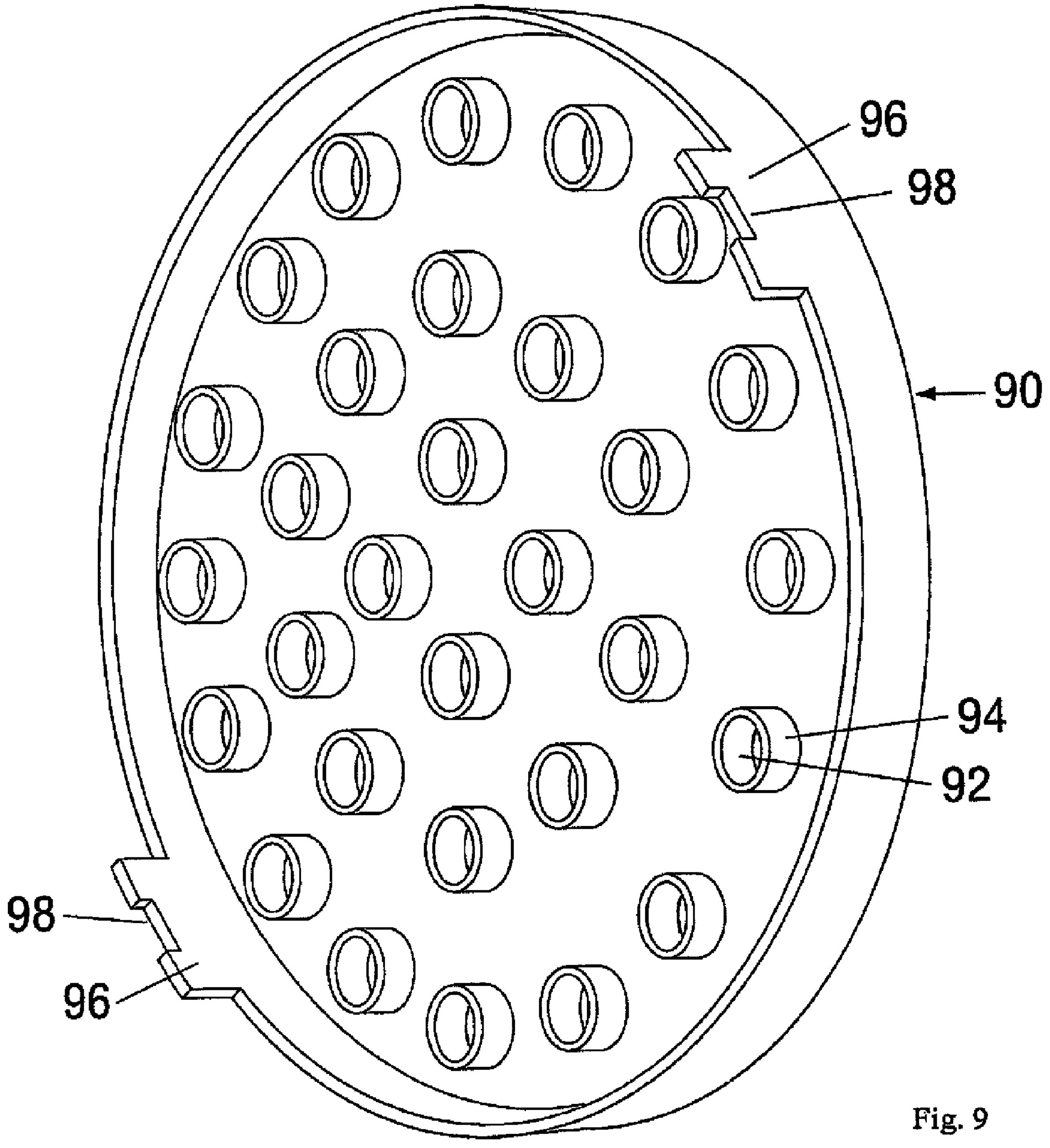
FIG. 9 is a perspective view of a guide plate according to one embodiment of the invention.

In another embodiment, the container may include a guide plate 90, as shown in FIG. 9, to assist in guiding a suppository dispensing tool into the surface openings 22 of the base 20. The guide plate 90 may be made of plastic, for example polypropylene, or other suitable materials as may be anticipated by one of ordinary skill in the art. The guide plate 90 may be shaped and sized to generally conform to the shape and size of the base 20, and may also include a plurality of guide plate openings 92 that correspond in number and size to the plurality of surface openings 22 on the base 20. The guide plate 90 may be placed onto the surface of the base 20 and positioned such that the guide plate openings 92 line up directly over the surface openings 22 of the base 20. The guide plate 90 may include one or more guide plate alignment tabs 96, each having an alignment tab groove 98, that may be aligned with one or more container alignment tabs 25 located on the container 10 to facilitate a proper alignment of each of the guide plate openings 92 with a corresponding surface opening 22 of the base 20. In a further embodiment, the guide plate 90 may also include guide plate opening projections 94 that may further assist in guiding the suppository dispensing tool through the guide plate 90 to the surface openings 22. In still another embodiment, the guide plate 90 may also include optional markings, as discussed above in relation to the base 20, in those embodiments when the guide plate 90 is used with the container 10 and, thus, covers up any optional markings that may exist on the surface of the base 20.

FIG. 2 depicts what may be described as a bottom side of the container 10, in relation to the perspective of FIG. 1, according to another embodiment of the invention. As shown, a plurality of hollow members 26 project from the underside of the base 20 within the lateral confines of the base support 24. In one embodiment, the hollow members 26 are cylindrical or tubular shaped structures positioned on the base 20 such that each hollow member 26 aligns with an opening 22 on the top side of the surface 20 (FIG. 1). In his manner, an object such as a compounded suppository inserted through a surface opening 22 of the base 20 may pass into the hollow member 26. As with the multiple shapes that the surface openings 22 can take within the scope of the invention, each of the hollow members 26 may also take the form of numerous shapes. The number of hollow members 26 that project from the base 20 may also vary, depending on the size of the container 10 and the number of suppositories desired for a dosage level. In any event, the number of hollow members 26 will correspond with the number of surface openings 22 on the base 20.

Figure 4:
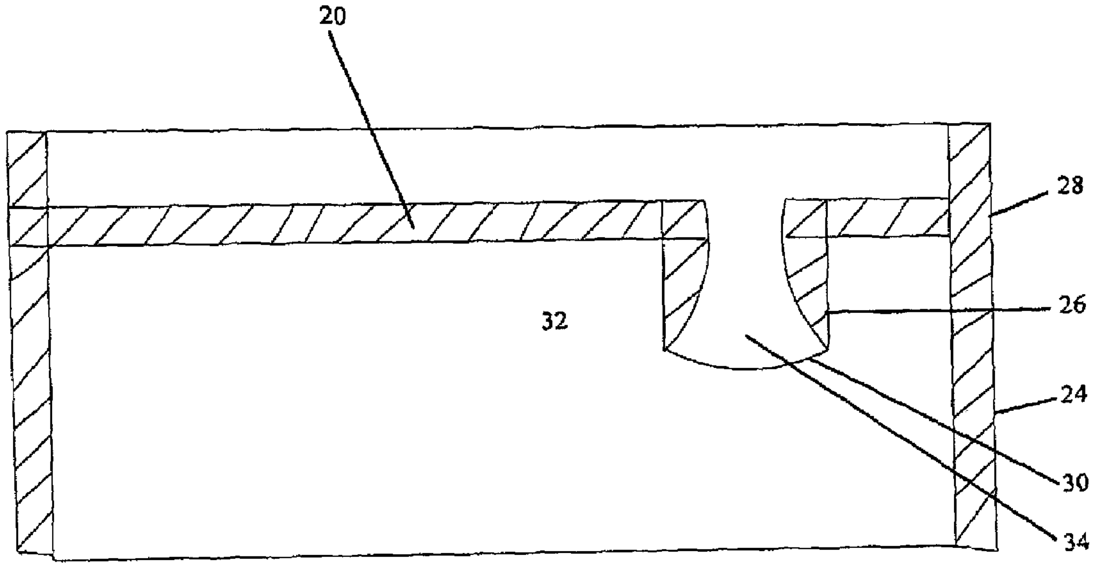
FIG. 4 is a cross-sectional view along the line 4-4 in FIG. 1, depicting only one exemplary hollow member for retaining suppositories.

FIG. 4 shows a cross-sectional view of the container 10, with the exception that it depicts only one exemplary hollow member 26 in cross-section. As shown in this embodiment, the hollow member 26 includes a top end, or first end, coincident with a surface opening 22 of the base 20, and a bottom end 30, or second end, that projects a distance from the top end and of the hollow member 26. In this embodiment, the external surface 32 of the hollow member 26 is generally tubular, as discussed above. As seen in cross-section, an internal surface 34 of the hollow member 26 may be shaped differently than the external surface 32. The internal surface 34 may, for example, project a conical or double-conical shape, torpedo or rocket shape, or a pencil shape. These exemplary shapes may be designed and incorporated into the internal dimensions of the hollow members 26 to facilitate the formation of a compounded suppository having a shape consistent with the internal surface 34 of the hollow member 26. Other shapes of the internal surface 34 of the hollow member 26 besides those described above are also within the scope of the present invention, as may be anticipated by one of ordinary skill in the art.

In another embodiment of the invention, the container 10 may include a barrier rim 28 that surrounds the base 20 and extends away from the base 20 as a projection from the base support 24. The barrier rim 28 may be advantageous in the preparation of compounded suppositories using the container 10 in that a mixture of drug and base added to the surface of the base 20 may be retained on the surface of the base 20 without spillage. In this manner, the barrier rim 28 may provide an improved ability to ensure that all of the drug/base mixture quantity ends up in the form of one or more suppositories, as opposed to some of the mixture being spilled from the surface of the base 20 and wasted, with the end result being an imprecise dosage amount for the suppositories.

However, it should be understood that in another embodiment of the invention, the container 10 has no barrier rim 28 integral with the container 10. The container 10 of the present invention may, for example, utilize a rim that is a separate sleeve, insertable over the container, to surround the base 20 and provide a retaining surface that may act to keep the volume of drug/base mixture added to the surface of the base 20 on the surface and prevent spillage. Alternatively, a rim may be formed by a separate device which is positioned around the container or in which the container is inserted.

Figure 5A:
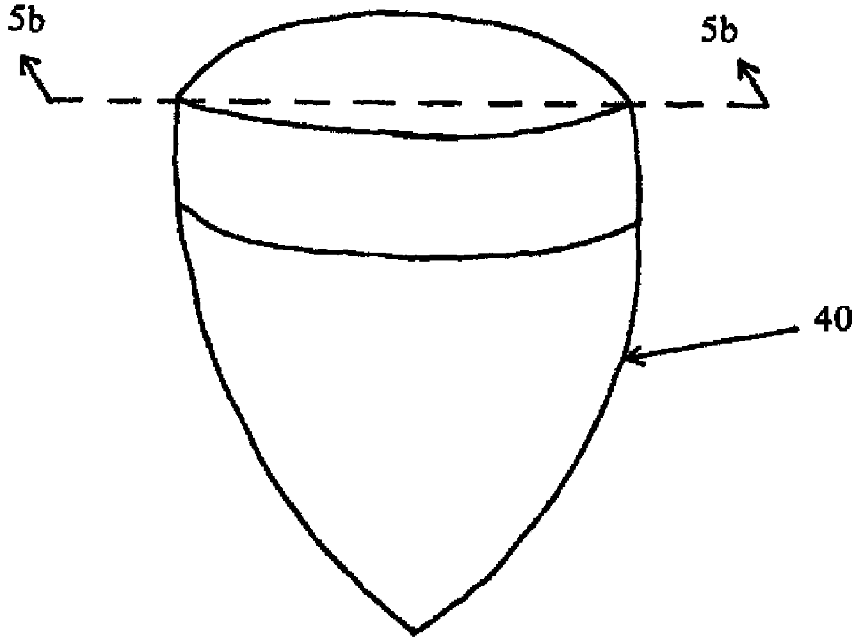
FIG. 5*a* is a perspective view of a cap according to one embodiment of the invention.
Figure 5B:
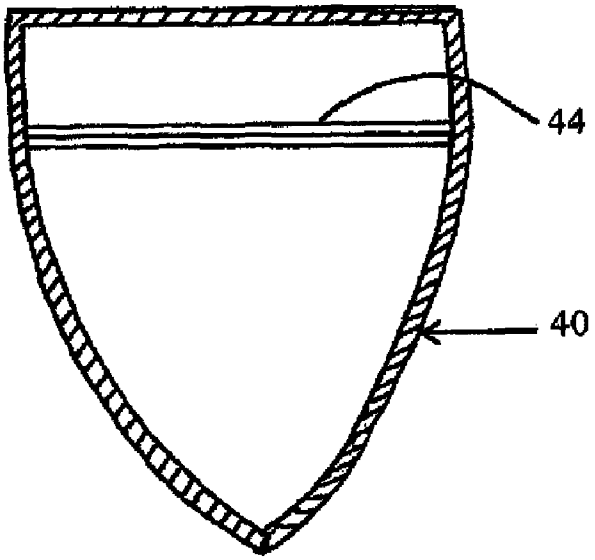
FIG. 5*b* is a cross-sectional view along line 5*b*-5*b* in FIG. 5*a;*

In another embodiment, a number of protective end covers, such as the removable caps 40 shown in FIGS. 5*a* and 5*b*, may be configured to be attachable or removably coupled to the bottom openings of the hollow members 26, as shown in FIG. 2. The removable caps 40 may be constructed and arranged to cover the bottom openings 30 of the hollow members 26, and thus allow a drug/base mixture that has been deposited through the base opening 22 into the hollow member 26 to build up and at least partially fill the hollow member 26. The removable caps 40 may also form a protective end around a suppository that has been solidified within the hollow member 26.

The shape of the protective end covers such as removable caps 40 may also dictate the shape of an end of a suppository prepared within the hollow member 26. In one embodiment, the removable caps 40 are generally conical in shape, resulting in a generally conically shaped end to such a prepared suppository. However, other shapes that may be used for the protective caps 40 include, but are not limited to, circular or noncircular dome shapes, pyramid shapes, and elliptical shapes. The removable caps 40 may be made of plastic and may include grooves 44 to facilitate a snap fit of the cap 40 over the end of hollow member 26. The caps 40 may also be sized to frictionally engage the internal surface 34 or external surface 32 of the hollow member 26 and thus be securable to the hollow member without requiring a snap fit. The caps 40 may also be made of rubber and may be sized so as to frictionally engage the internal surface 34 or external surface 32 of the hollow member 26 to close the bottom opening 30 of the hollow member 26. Rubber caps that snap fit onto the end of the hollow members 26 are also anticipated by this invention.

Figure 8:
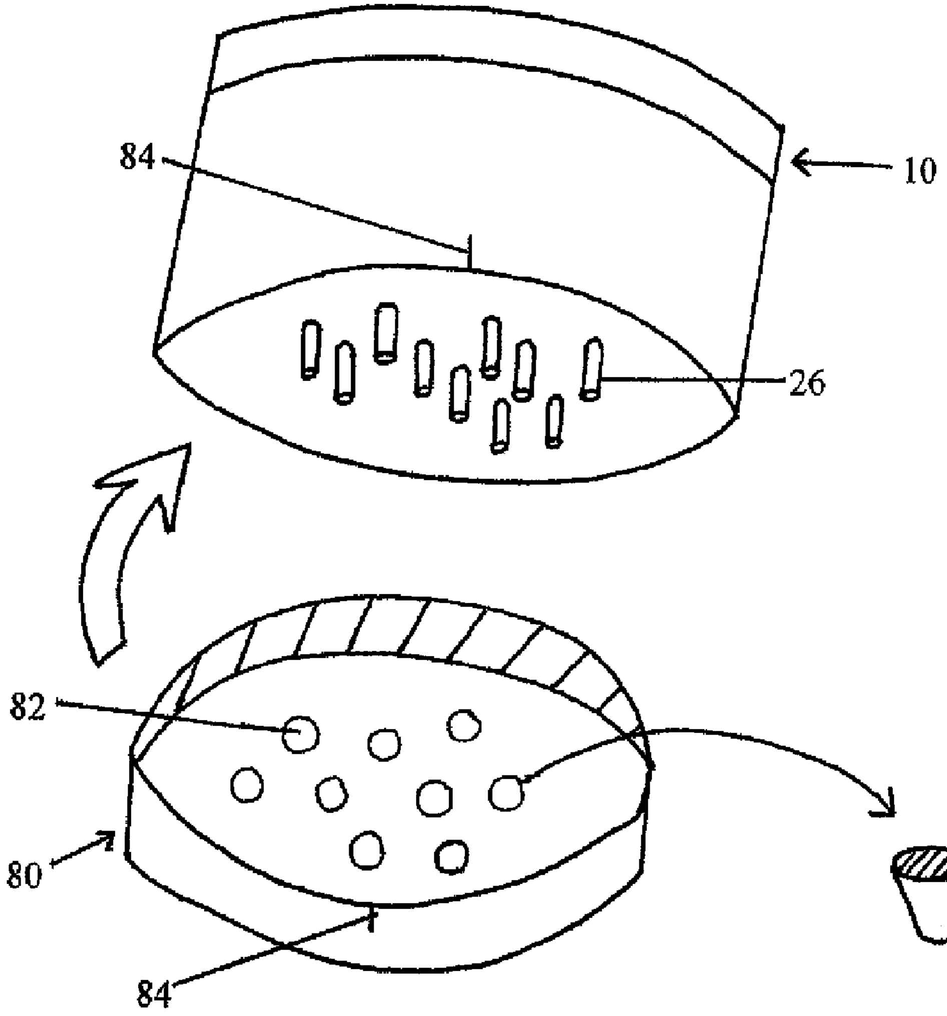
FIG. 8 is a perspective view of a bottom protective cover in conjunction with the container of FIG. 1.
Figure 8A:
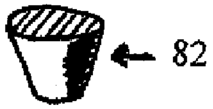
FIG. 8*a* is a perspective view of an exemplary protective shell from FIG. 8.

Other types of protective end covers within the scope of this invention include sleeves that extend through the hollow members 26 and protrude from the second opening. In another embodiment, as depicted in FIG. 8, protective shells 82 (shown in further detail in FIG. 5*a*) may be formed in the surface of a bottom protective cover 80 that may be coupled to the bottom side of the container 10. The bottom protective cover 80 and the bottom side of the container 10 may also each include guiding grooves 84 that may aid in properly aligning the bottom protective cover 80 such that each of the bottom openings 30 of hollow members 26 are covered by a protective shell 82.

The container of the present invention may also be constructed and arranged such that different sizes, shapes and types of suppositories may be prepared, stored and dispensed from the same container. As such, the container may have one portion in which the guide plate openings 92, surface openings 22, hollow members 26 and protective end covers of that container portion are shaped, sized or otherwise arranged to facilitate the preparation of one type of suppository, while one or more other portions of the container may have guide plate openings 92, surface openings 22, hollow members 26 and protective end covers shaped, sized or otherwise arranged to facilitate the preparation of another type of suppository, all within the same container at the same time. In another embodiment, the hollow members 26, surface openings 22, guide plate openings 92 and/or the protective end covers, such as removable caps 40, may be colored coded or otherwise marked in a desired manner to make it easier for a suppository preparer or end user to readily identify distinctions between different suppositories that may have been prepared and stored in a single container.

Figure 6A:
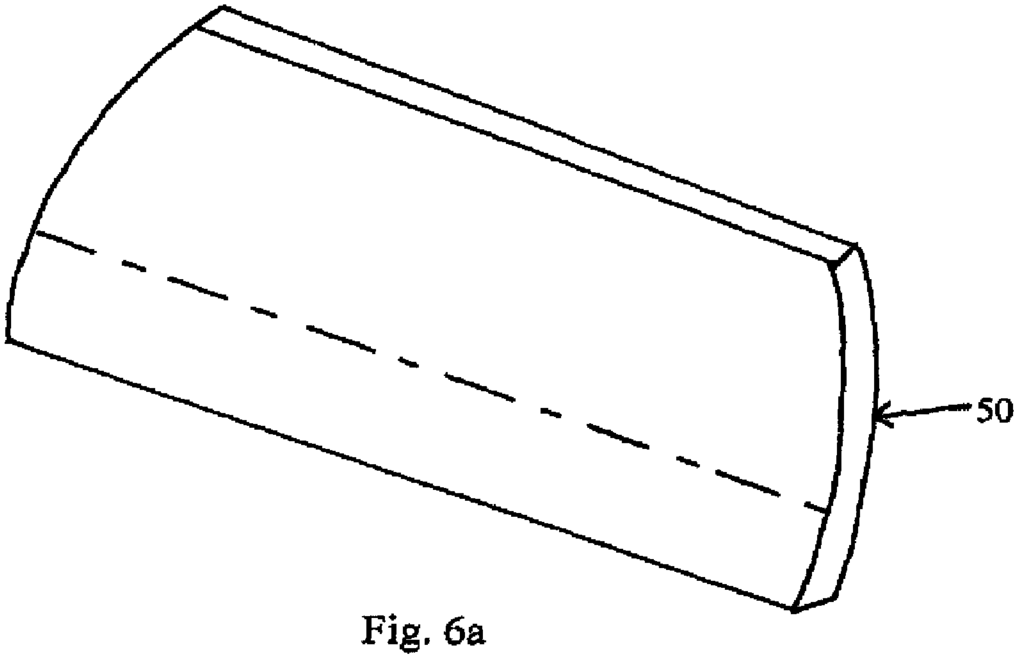
FIG. 6*a* is a perspective view of a suppository filling tool according to one embodiment of the invention.
Figure 6B:
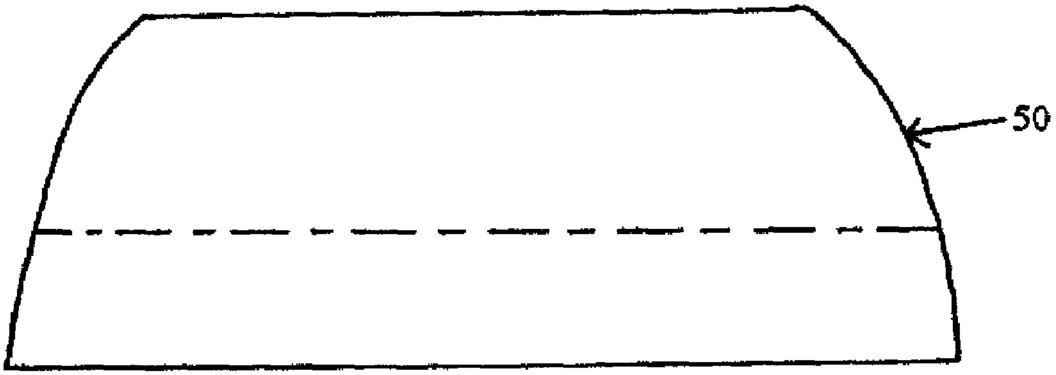
FIG. 6*b* is a front plan view of the suppository filling tool of FIG. 6*a;*
Figure 7A:
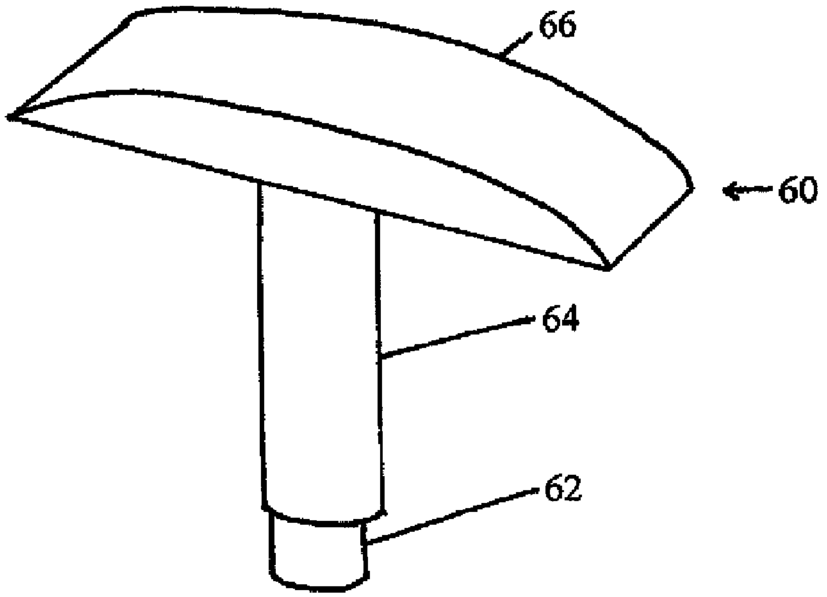
FIG. 7*a* is a perspective view of a suppository dispensing tool according to one embodiment of the invention.
Figure 7B:
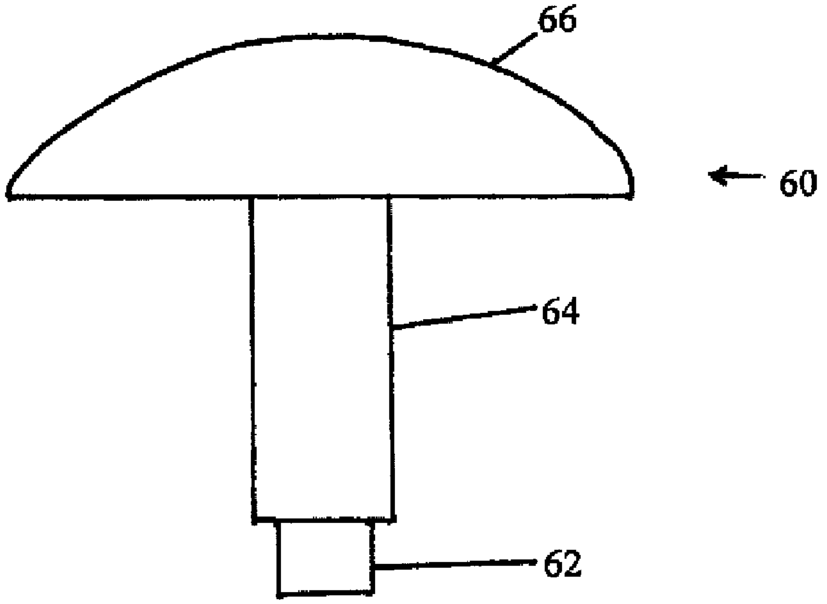
FIG. 7*b* is a front plan view of the suppository dispensing tool of FIG. 7*a;*

The container 10 may also be part of a suppository kit that is used to prepare, store and dispense suppositories. The kit may include at least some of the following items: one or more drugs to be compounded; a base with which to mix the drug to form the suppository dosage; a suppository container, such as the container 10 of FIGS. 1-2; protective end covers that are engageable with hollow members to aid in the forming of suppositories, such as the protective caps 40 of FIGS. 5*a* and 5*b*; a plunger-type device, such as the suppository dispensing tool device 60 depicted in FIGS. 7*a* and 7*b*; and a suppository filling tool, such as the suppository filling tool 50 in FIGS. 6*a* and 6*b*. The kit may also come with instructions for a pharmacist or other medical authority in how to prepare these suppositories as well as instructions for storage and dispensing of the suppositories by an end user.

In preparing one or more suppositories using a container such as the container 10 of FIGS. 1 and 2, a pharmacist or the like may mix a prescribed dosage of one or more drugs with a melted base in a quantity sufficient to create the desired number of compounded suppositories. The drug and base mixture may then be added to the base 20 of the container 10 such that the rim 28 may keep the drug and the base mixture within the confines of the container 10. A suppository filling tool 50 may then be used to spread the drug and base mixture across the surface of the base 20, and in so doing causes the drug and base mixture to pass through the openings 22 of the base 20 and into the hollow members 26 projecting below the base 20.

After all of the drug and base mixture is removed from the surface of the base 20 with the aid of the suppository filling tool 50, the container may then be cooled to harden the drug and base mixture in the hollow members 26 into a solid form. The protective caps 40 removably coupled to the bottom end 30 of the hollow members 26 may, along with the internal surface 34 of the hollow members 26, aid in forming the desired shaped suppository in solid form. The suppositories may then be stored by the pharmacist or medical professional in the same container 10 in which they were prepared, without requiring any direct handling of the actual suppositories.

This same container 10 may then be passed along to a patient or end user for further storage and subsequent dispensing of the suppositories, which may be dispensed one at a time with minimal to no direct handling of the suppository until it is ready to be administered to the patient. To dispense one or more suppositories, the user may utilize a plunger-like device, such as the suppository dispensing tool 60 shown in FIGS. 7*a* and 7*b*, to eject the suppositories from the hollow cylinders 26. By inserting the plunging end 62 of the suppository dispensing tool 64 through guide plate openings 92 of the guide plate 90 and into the opening 22 of the base 20, the user may eject a suppository from the container for individual administering to the body. The user may hold the holding end 66 during the process. The user may then separate the removable cap 40 from the ejected suppository prior to administering the suppository dosage.

The present invention is further illustrated by the following Examples, which are not to be construed as limiting the scope of the invention in any manner.

EXAMPLES

Example 1

Table II sets forth examples of successful preparation, storage and dispensing of suppositories with varied drug and base combinations, and different concentrations of drugs, all using an embodiment of the container of the present invention. For this example, a 30-suppository container of the present invention was utilized for each of the compounded combinations described below.

TABLE II

| Successful Drug and Base Combinations |
|---|
| 1. 100 mg Progesterone using Weecobee M |
| 2. 100 mg Progesterone using Hydrokote M |
| 3. 100 mg Progesterone using PolyethyleneGlycol 1450 NF, Base A |
| 4. 50 mg Progesterone using Weecobee M |
| 5. 50 mg Progesterone using Hydrokote M |
| 6. 50 mg Progesterone using Polyethylene Glycol 1450 NF, Base A |
| 7. 200 mg Progesterone using Weecobee M |
| 8. 25 mg Progesterone using Weecobee M |

TABLE II-continued

| Successful Drug and Base Combinations |
|---|
| 9. 100 mg Lidocaine HCl using Weecobee M |
| 10. 100 mg Ketoprofen using Weecobee M |
| 11. 500 mg Metronidazole using Weecobee M |
| 12. 100 mg Hydrocortisone using Weecobee M |
| 13. 25 mg Promethazine using Weecobee M |
| 14. 100 mg Hydrocortisone and 44 mg Lidocaine using Weecobee M, |
| 15. 600 mg Boric acid using Weecobee M |
| 16. 300 mg Boric acid using Weecobee M |

The progesterone/Weecobee M formulation (1) is made as follows: 67.88 grams of Weecobee M (purchased from Stepan Company, Northfield, Ill.) is heated to melting. This can be accomplished in a water bath, microwave, or the like. Weecobee M will melt at approximately 40-45° C. although it can be heated to higher temperature (e.g., 100° C.) without significant effect. Once the Weecobee M is melted, a mixture of 3.3 grams progesterone and 0.82 grams silica gel (both purchased from Spectrum Pharmacy Products, Tucson, Ariz.) is added, keeping the mixture warm and gently stirring. Once the progesterone/silica gel mixture is dissolved/dispersed or suspended in the Weecobee M base (approximately 2 minutes) and while the entire mixture is still molten, the entire mixture is poured onto the container. There are approximately 2.2 grams of mixture (from an initial total of 72 grams) in each suppository. This method is intended for 30 suppositories. There is expected to be some loss of mixture in the preparation and in the residue in the container that does not get into the individual suppository molds. Accordingly, it is advisable to start with approximately 5-10% more mixture than is actually needed to account for this anticipated loss of material.

The same experiment was performed with the exception that the silica gel was not added to the mixture. The amount of base was increased to account for the decreased weight occurring from the lack of silica gel in the mixture. The suppositories resulting from the silica gel were well formed and had less of a yellow tint than the suppositories made with silica gel. Thus in some embodiments it is more preferred to produce the suppositories without silica gel.

A similar strategy can be used to make the remaining formulations, except that the Weecobee M is replaced with the different bases and progesterone is replaced with the different drugs. Each of these formulations is intended to make 30 suppositories.

Results: Each of the 30 suppositories created for each of the 16 exemplary combinations described above were able to be dispensed from the container without fracture or deformation and were consistent in shape, color, size and appearance. Additionally, each of the suppositories had a dispensed weight of between 2.10-2.28 grams.

Example 2

100 milligram Progesterone suppositories were prepared with or without silica, stored in two groups at temperatures of (1) 25° C. and (2) 4° C., and dispensed on a periodic basis over a 120 day period using an embodiment of the container of the present invention. The suppositories stored at each temperature were dispensed and inspected on days 1, 7, 12, 28, 35, 48, 70, and 120 following the day of suppository preparation.

Results: Each of the suppositories, at either temperature, were able to be dispensed with ease and upon inspection showed consistent appearance and shape, and weighed between 2.10-2.28 grams.

Example 3

A weight comparison was made between suppositories prepared with or without silica using a container of the present invention, and control suppositories prepared using (1) a commercially available metal mold, and (2) a commercially available disposable plastic shell. For this weight comparison, both the metal mold and the disposable plastic shell were purchased from Spectrum Pharmacy Products, Tucson, Ariz. Three groups (container, metal mold, plastic shell) of 10 suppositories each were prepared from 100 milligrams of Progesterone and a base of Weecobee M Results: The 10 suppositories prepared using a container of the present invention had weights ranging between 2.0-2.2 grams. The 10 suppositories prepared using the metal mold had weights ranging between 1.4-1.7 grams. The 10 suppositories prepared using the plastic shells had weights ranging between 1.8-2.2 grams While the invention has been described with reference to various illustrative embodiments and examples, the invention is not limited to the embodiments described. It is evident that many alternatives, modifications and variations of the embodiments described will be apparent to those of ordinary skill in the art. Accordingly, embodiments of the invention as set forth herein are intended to be illustrative, and not limiting the scope of the invention. Various changes may be made without departing from the scope of the invention.

What is claimed is:

1. A method of preparing compounded suppositories, comprising:

providing a container having a surface with a plurality of openings dispersed across the surface, each of the openings forming a first end of each of a plurality of hollow members, each of the hollow members extending from the surface to a second end of the hollow member;

adding a suppository mixture of at least one drug and at least one suppository base to the surface of the container;

spreading the suppository mixture across the surface such that the mixture falls through the plurality of openings dispersed across the surface and into the plurality of hollow members, forming a plurality of compounded suppositories;

storing the compounded suppositories in the container, and further comprising dispensing the suppository from at least one of the plurality of hollow members, wherein dispensing the suppository from at least one of the plurality of hollow members comprises ejecting the suppository from the hollow member by inserting a suppository dispensing tool into the first end of the hollow member to force the suppository from the second end of the hollow member.

2. The method of claim 1, wherein the surface is a substantially planar surface.

3. The method of claim 1, wherein the second end of the hollow member comprises a cap removably coupled to the second end and dispensing the suppository further comprises removing the cap from the second end of the hollow member.

4. The method of claim 1, wherein the drug is selected from the group consisting of Progesterone, Boric Acid, Morphine and Indomethacin.

5. The method of claim 1, wherein the suppository base is selected from the group consisting of Weecobee M, Hydrokote M, and Polyethylene Glycol 1450 NF, Base A.

* * * * *